United States Patent
Su et al.

(10) Patent No.: US 7,169,268 B2
(45) Date of Patent: Jan. 30, 2007

(54) COLOR STABILIZATION OF AMINES

(75) Inventors: Wei-Yang Su, Austin, TX (US); Mark L. Posey, Austin, TX (US); Maarten P. ter Weeme, Spring, TX (US)

(73) Assignee: Huntsman Petrochemical Corporation, The Woodlands, TX (US)

( * ) Notice: Subject to any disclaimer, the term of this patent is extended or adjusted under 35 U.S.C. 154(b) by 0 days.

(21) Appl. No.: 10/456,655

(22) Filed: Jun. 6, 2003

(65) Prior Publication Data

US 2004/0000471 A1    Jan. 1, 2004

Related U.S. Application Data

(60) Provisional application No. 60/391,754, filed on Jun. 26, 2002.

(51) Int. Cl.
*B01D 3/34* (2006.01)
*C07C 209/82* (2006.01)

(52) U.S. Cl. .............. 203/6; 203/38; 203/59; 203/78; 564/497

(58) Field of Classification Search .......... 203/2, 203/6, 29, 38, 59, 78, 100; 564/497, 499
See application file for complete search history.

(56) References Cited

U.S. PATENT DOCUMENTS

| | | | |
|---|---|---|---|
| 3,567,779 A | 3/1971 | Currier et al. | 260/584 |
| 4,567,303 A | 1/1986 | Boettger et al. | 564/475 |
| 4,609,436 A * | 9/1986 | Bakkum | 203/6 |
| 4,731,165 A | 3/1988 | Niebruegge et al. | 203/29 |
| 4,766,247 A | 8/1988 | Ford et al. | 564/498 |
| 4,806,229 A * | 2/1989 | Ferguson et al. | 208/47 |
| 5,663,444 A | 9/1997 | Melder et al. | 564/477 |

FOREIGN PATENT DOCUMENTS

| | | |
|---|---|---|
| DE | 4414879 | * 11/1995 |
| EP | 0 028 555 | 6/1983 |

* cited by examiner

*Primary Examiner*—Virginia Manoharan
(74) *Attorney, Agent, or Firm*—Ron D. Brown; Edward Korompai

(57) ABSTRACT

The present invention concerns a process for providing tertiary amine products which are color-stable, and have a greatly reduced tendency to take on color during their storage. According to the invention, an ethyleneamine derivative is added to the distillation pot prior to or during the distillation of the tertiary amine product. Preferably, the ethyleneamine derivative has a higher boiling point than the desired tertiary amine product so as to preclude the ethyleneamine from distilling over with the tertiary amine.

5 Claims, No Drawings

COLOR STABILIZATION OF AMINES

CROSS-REFERENCES TO RELATED APPLICATIONS

This Application claims priority to U.S. patent application Ser. No. 60/391,754 filed Jun. 26, 2002 which is currently still pending.

FIELD OF THE INVENTION

The present invention relates generally to processes for producing amine products. More particularly, it relates to processes for producing amines having a reduced tendency to change color during storage over the passage of time.

BACKGROUND INFORMATION

Many organic amines in their purest forms are typically water-white, liquid substances in appearance. However, owing to the presence of one or more impurities present or formed during the manufacturing or processing of amines, amine products are well-known to often have the tendency to take on color over the course of time, for example, by virtue of their having been contained in a storage tank or other containment vessel. Typically, amines turn brown with the passage of time.

In general, amines can be decolorized to become a color-stable product by hydrogenation, or by treatment with activated carbon or acid, followed by distillation. However, the extra processing steps so required result in yield loss, and add overall cost to a product so treated. Other methods for decolorizing or otherwise providing color-stable amine products have been described by various workers as well.

For example, U.S. Pat. No. 5,663,444 teaches a process for the preparation of a color-stable dialkylaminoethanol of the formula:

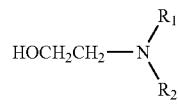

in which $R_1$ and $R_2$ independently are $C_1$–$C_{20}$-alkyl, by reacting ethylene oxide with a dialkylamine of the formula $HNR_1R_2$, in which $R_1$ and $R_2$ have the same meaning, in the presence of from 2.5 to 50% by weight of water, based on the reaction mixture, at a temperature of from 95° to 170° C., and separating off the water and high-boiling constituents by distillation under a reduced pressure and at a temperature of from 40° to 90° C. at the column bottom.

U.S. Pat. No. 4,567,303 discloses a process for preparing colorless alkanolamines and/or alkylenediamines which comprises thermally reacting ammonia (or a reactive amine and an alkylene oxide or alkanolamine) in a reactor in which the corrosion-sensitive parts of the reactor are made of substantially nickel-free stainless steel.

U.S. Pat. No. 3,567,779 provides a method for stabilizing amines against color change at reflux boiling temperatures by incorporating in the amine a stabilizing amount of a mono- or di-lower alkanolamine.

U.S. Pat. No. 4,766,247 discloses a process for the reduction of the color of polyamines by reacting at elevated temperature, i.e. 50° to 175° C., and pressure, i.e. 50 to 1500 psig, such colored polyamines, e.g. triethylenetetramine or tetraethylenepentamine, in the presence of a hydrogenation catalyst, e.g. Raney nickel or palladium on carbon, and a hydrogen atmosphere for a period of time sufficient to effectuate the desired reduction in color. The polyamines can either be distilled into a narrow product composition and then hydrogenated or a crude polyamine product can be hydrogenated and then distilled to produce the desired product composition.

U.S. Pat. No. 4,731,165 teaches a process of de-coloring crude triethylenetetramine (TETA) is disclosed. In the disclosed and preferred procedure, a sulfonic acid ion exchange resin acts on the crude TETA to enable subsequent distillation at elevated temperature to obtain de-colored TETA.

European Patent EP 0 028 555 teaches the purification of dialkylaminoethanols by subjecting them to catalytic hydrogenation treatment in the heterogeneous phase prior to distillation.

SUMMARY OF THE INVENTION

The present invention provides processes to produce color-stable amines by treating an amine which is prone to change color over time during storage with an ethylenediamine derivative during the distillation of the desired amine product. The process of the invention is particularly well-suited for the preparation of color-stable tertiary amines in general, and particularly tertiary amines which include at least one alkanol appendage.

Thus, the present invention is a process which comprises the steps of providing a tertiary amine product represented by the chemical structure:

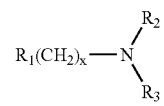

in which x may be any integer between 1 and 8, including 1 and 8; wherein $R_1$ may be hydrogen, hydroxy, or the group:

wherein Y may be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8; and wherein Z may be may be: i) hydrogen; ii) any alkyl group, whether straight-chain, branched, or cyclic containing between 1 and 10 carbon atoms, including 1 and 10; iii) the group—$(CH_2)_xOH$ in which x may be any integer between 1 and 8, including 1 and 8; or iv) an aminoalkyl group defined by the formula:

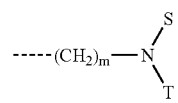

in which m may be any integer between 1 and 6, including 1 and 6; and S and T are each independently selected from the group consisting of: hydrogen, or any $C_1$ to $C_6$ alkyl group; and $R_2$ and $R_3$ may each independently be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8, into the pot portion of a distillation apparatus, along with a minor amount of an ethyleneamine derivative selected from the group consisting of: ethylenediamine; aminoethylethanolamine; diethylenetriamine; triethylenetetramine; tetraethylenepentamine; pentaethylenehexamine; 1,2-propylenediamine; N-(2-hydroxypropyl)ethylenediamine; N-(2-hydroxybutyl)ethylenediamine; N-(2-hydroxyethyl)-1,2-propylenediamine; N-(2-hydroxypropyl)-1,2-propylenediamine; and N-(2-hydroxybutyl)-1,2-propylenediamine, and distilling the mixture, and collecting that fraction of the distillation over which the desired tertiary amine product is normally collected.

DETAILED DESCRIPTION OF THE INVENTION

Tertiary amines are prone to turning yellow or brown during their storage. This is usually attributable to unknown impurities which form over time. We have found that by adding an ethyleneamine derivative to the last tower of the purification distillation train during the purification of a tertiary amine product, that a color-stable tertiary amine product is produced.

Ethyleneamine derivatives suitable for use as additives to the final distillation of a tertiary amine product may be any amine selected from the group consisting of: ethylenediamine; aminoethylethanolamine; diethylenetriamine; triethylenetetramine; tetraethylenepentamine; pentaethylenehexamine; 1,2-propylenediamine; N-(2-hydroxypropyl)ethylenediamine; N-(2-hydroxybutyl)ethylenediamine; N-(2-hydroxyethyl)-1,2-propylenediamine; N-(2-hydroxypropyl)-1,2-propylenediamine; and N-(2-hydroxybutyl)-1,2-propylenediamine.

In practice of a process according to the invention, a minor amount of an ethyleneamine derivative is added to the pot in which the distillation of the desired tertiary amine product is carried out, prior to the commencement of the distillation. The ethyleneamine derivative is preferably present in any amount between about 0.001 and about 20% percent by weight, including without limitation every amount therebetween, including every thousandth percentage therebetween, based upon the total amount of desired tertiary amine product present in the pot at the commencement of the distillation. Preferably, the ethyleneamine derivative is present in any amount between about 0.05% and about 2% percent by weight, including without limitation every amount therebetween, based upon the total amount of desired tertiary amine product present in the pot at the commencement of the distillation. More preferably still, the ethyleneamine derivative is present at about 1.00% by weight based upon the total amount of desired tertiary amine product present in the pot at the commencement of the distillation. In a preferred embodiment, the total amount of ethyleneamine derivative relative to the desired tertiary amine product is maintained constant throughout the distillation, as in a continuous distillation process.

Preferably, the ethyleneamine derivative and the tertiary amine product desired are both liquid at the time of their being combined, which is conducted by simple admixture of the liquids. Conveniently, the desired tertiary amine product may be heated to just below its boiling point in a distillation pot, and the ethyleneamine derivative subsequently added to the pot prior to commencing the distillation.

Tertiary amine products for purposes of this invention and the appended claims are those represented by the chemical structure:

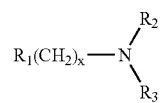

in which x may be any integer between 1 and 8, including 1 and 8; wherein $R_1$ may be hydrogen, hydroxy, or the group:

wherein Y may be: i) hydrogen; ii) any alkyl group, whether straight-chain, branched, or cyclic containing between 1 and 10 carbon atoms, including 1 and 10; or iii) the group—$(CH_2)_xOH$, in which x may be any integer between 1 and 8, including 1 and 8; and wherein Z may be may be: i) hydrogen; ii) any alkyl group, whether straight-chain, branched, or cyclic containing between 1 and 10 carbon atoms, including 1 and 10; iii) the group—$(CH_2)_xOH$ in which x may be any integer between 1 and 8, including 1 and 8; or iv) an aminoalkyl group defined by the formula:

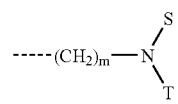

in which m may be any integer between 1 and 6, including 1 and 6; and S and T are each independently selected from the group consisting of hydrogen, or any $C_1$ to $C_6$ alkyl group; and $R_2$ and $R_3$ may each independently be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8.

The examples which now follow are illustrative of the invention and should not be considered as being delimitive thereof in nay way whatsoever.

EXAMPLE 1

Color-Stabilization of DMEA—About 1700 g of crude dimethylethanolamine (DMEA) from the plant was added 17 g of aminoethylethanolamine (AEEA) and was distilled at 100 mmHg. Low color DMEA with the color of Pt—Co 4.7 was obtained.

EXAMPLE 2

Color-Stabilization of DMEA—The procedure of Example 1 was followed except that 8.5 g of AEEA was added. Low color DMEA with the color of Pt—Co 8.5 was obtained.

EXAMPLE 3

Comparison Study

The procedure of Example 1 was followed except the no AEEA was added. DMEA with color of Pt—Co 25.5 was obtained.

EXAMPLE 4

Color Stability Test

DMEA from the examples above were test for color stability. The samples were put in an oven at 100° C. for four hours under a nitrogen atmosphere in one set, and under an air atmosphere in a second set. The color was then measured using the Pt—Co color scale, the values of which for each of the readings are tabulated below:

| Sample ID | Original | Nitrogen atmosphere | Air atmosphere |
|---|---|---|---|
| Example 1 | 4.7 | 8.3 | 22.7 |
| Example 2 | 8.5 | 14.7 | 51 |
| Example 3 | 25.5 | 53.1 | 102.2 |

These results show that adding AEEA into the last distillation tower results in color-stable DMEA product.

Preferably, the ethyleneamine derivative is selected so that its boiling point is higher than that of the desired tertiary amine product, so as to thus preclude the presence of the ethyleneamine derivative in the distillate, which would constitute an impurity therein. However, the present invention contemplates selecting the ethyleneamine derivative to have a lower boiling point than that of the desired tertiary amine product, when the distillation apparatus is configured to recycle the light boilers (in this case the ethyleneamine derivative) back into the feed stream in a continuous process while simultaneous distilling the desired tertiary amine product at another location in the column.

Although the present process has been described in terms of its being a batch process, the present invention contemplates employment of the inventive principles herein in analogous continuous processes, which are well-known in the art of distillation.

A process according to the invention may be operated using conventional temperatures and pressures employed for purification of amine products by distillation. One of ordinary skill in the art will recognize upon reading and understanding this specification and the appended claims that distillations for purifying tertiary amine products according to the present invention may utilize either atmospheric, superatmospheric, or subatmospheric pressures, as the adjustment of pressure for a distillation procedure and the required attendant adjustment in temperature are process variables well within the level of skill of the ordinary distillation artisan.

In one preferred form of the invention, the desired tertiary amine product which is to be decolorized is substantially pure prior to its being distilled in the presence of added ethyleneamine derivative. In one preferred form of the invention, the tertiary amine product which is to be decolorized is at least 50% pure prior to its being distilled in the presence of added ethyleneamine according to the invention. In another preferred form of the invention, the tertiary amine product which is to be decolorized is at least 60% pure prior to its being distilled in the presence of added ethyleneamine according to the invention. In yet another preferred form of the invention, the tertiary amine product which is to be decolorized is at least 70% pure prior to its being distilled in the presence of added ethyleneamine according to the invention. In yet another preferred form of the invention, the tertiary amine product which is to be decolorized is at least 80% pure prior to its being distilled in the presence of added ethyleneamine according to the invention. In yet another preferred form of the invention, the tertiary amine product which is to be decolorized is at least 90% pure prior to its being distilled in the presence of added ethyleneamine according to the invention. It is most preferred that the tertiary amine product which is to be decolorized is at least 95.00% pure prior to its being distilled in the presence of added ethyleneamine according to the invention. Thus, the feedstock tertiary amine may be of varying degrees of purity prior to its being processed according to the invention.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the present invention is intended to cover all such modifications and alterations, and is limited only by the scope of the claims which now follow.

What is claimed is:

1. A process for producing a color-stable tertiary amine product comprising the steps of:
   a) providing a distillation apparatus having a boiling pot portion, a condenser, and receiver, wherein the distillation apparatus comprises a last tower of a distillation train;
   b) feeding a major amount of a desired tertiary amine product in said boiling pot, said tertiary amine having the chemical structure:

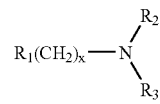

in which x may be any integer between 1 and 8, including 1 and 8; wherein $R_1$ may be hydrogen, hydroxy, or the group:

wherein Y may be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8; and wherein Z may be: i) hydrogen; ii)

any alkyl group, whether straight-chain, branched, or cyclic containing between 1 and 10 carbon atoms, including 1 and 10; iii) the group—$(CH_2)_xOH$ in which x may be any integer between 1 and 8, including 1 and 8; or iv) an aminoalkyl group defined by the formula:

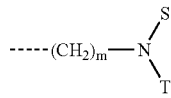

in which m may be any integer between 1 and 6, including 1 and 6; and S and T are each independently selected from the group consisting of: hydrogen, or any $C_1$ to $C_6$ alkyl group; and $R_2$, and $R_3$ may each independently be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8;

c) feeding a minor amount of an ethyleneamine derivative which has a boiling point higher than said desired tertiary amine product at standard temperature and pressure, said ethyleneamine derivative being selected from the group consisting of: ethylenediamine; aminoethylethanolamine; diethylenetriamine; triethylenetetramine; tetraethylenepentamine; pentaethylenehexamine; 1,2-propylenediamine; N-(2-hydroxypropyl)ethylenediamine; N-(2-hydroxybutyl)ethylenediamine; N-(2-hydroxyethyl)-1,2-propylenediamine; N-(2-hydroxypropyl)-1,2-propylenediamine; and N-(2-hydroxybutyl)-1,2-propylenediamine in said boiling pot of said last tower;

d) distilling said desired tertiary amine product and said ethyleneamine derivative by providing heat to said boiling pot portion so as to cause vaporization of said desired tertiary amine product and its subsequent condensation in said condenser to produce the color-stable tertiary amine product, wherein said distilling provides final distillation of said desired tertiary amine product; and e) collecting said color-stable tertiary amine product in said receiver, wherein said ethyleneamine derivative is present in said pot portion in any amount between about 0.001% and about 20% by weight based on the total amount of tertiary amine present in said pot portion.

2. A process according to claim 1 wherein the difference between the boiling point of said desired tertiary amine product and said ethyleneamine derivative is at least five degrees Centigrade.

3. A process according to claim 1 wherein the difference between the boiling point of said desired tertiary amine product and said ethyleneamine derivative is ten degrees Centigrade or more.

4. A process according to claim 1 wherein said tertiary amine is selected from the group consisting of: methyldiethanolamine, N,N-dimethylethanolamine, bis-(2-dimethylaminoethyl) ether, pentamethyldiethylenetriamine, 2-(2-dimethylaminoethoxy) ethanol, triethylamine, and N,N,N'-trimethyl-N'-hydroxyethyl-bisaminoethylether.

5. A process for producing a color-stable tertiary amine product comprising the steps of:

a) providing a distillation apparatus having a boiling pot portion, a condenser, and a receiver, wherein the distillation apparatus comprises a last tower of a distillation train;

b) feeding a major amount of a desired tertiary amine product in said boiling pot, said tertiary amine having the chemical structure:

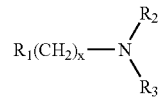

in which x may be any integer between 1 and 8, including 1 and 8; wherein $R_1$ may be hydrogen, hydroxy, or the group:

wherein Y may be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8; and wherein Z may be: i) hydrogen; ii) any alkyl group, whether straight-chain, branched, or cyclic containing between 1 and 10 carbon atoms, including 1 and 10; iii) the group—$(CH_2)_xOH$ in which x may be any integer between 1 and 8, including 1 and 8; or iv) an aminoalkyl group defined by the formula:

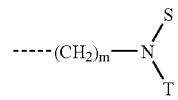

in which m may be may be any integer between 1 and 6, including 1 and 6; and S and T are each independently selected from the group consisting of: hydrogen, or any $C_1$ to $C_6$ alkyl group; and $R_2$, and $R_3$ may each independently be: i) hydrogen; ii) any alkyl group, whether straight-chain, branched, or cyclic containing between 1 and 10 carbon atoms, including 1 and 10; or iii) the group—$(CH_2)_xOH$ in which x may be any integer between 1 and 8, including 1 and 8;

c) feeding a minor amount of an ethyleneamine derivative which has a boiling point that is lower than said desired tertiary amine product at standard temperature and pressure, said ethyleneamine derivative being selected from the group consisting of: ethylenediamine; aminoethylethanolamine; diethylenetriamine; triethylenetetramine; tetraethylenepentamine; pentaethylenehexamine; 1,2-propylenediamine; N-(2-hydroxypropyl)ethylenediamine; N-(2-hydroxybutyl)ethylenediamine; N-(2-hydroxytheyl)-1,2-propylenediamine; N-(2-hydroxypropyl)-1,2-propylenediamine; and N-(2-hydroxybutyl)-1,2-propylenediamine in said boiling pot of said last tower;

d) distilling said desired tertiary amine product and said ethyleneamine derivative by providing heat to said boiling pot portion so as to cause vaporization of said desired tertiary amine product and its subsequent condensation in said condenser to produce the color-stable tertiary amine product, wherein said distilling provides final distillation of said desired tertiary amine product; and e) collecting said color-stable tertiary amine product in said receiver, wherein said ethyleneamine derivative is present in said pot portion in any amount between about 0.001% and about 20% by weight based on the total amount of tertiary amine present in said pot portion, and wherein the distillation apparatus is configured to continuously recycle the ethyleneamine to a feed to the distillation apparatus, while simultaneously distilling the desired tertiary amine product at a different location in the colunm.

* * * * *